(12) United States Patent
Steele

(10) Patent No.: US 10,959,820 B1
(45) Date of Patent: Mar. 30, 2021

(54) CHEEK RETRACTION DEVICE

(71) Applicant: Dallas B. Steele, Phoenix, AZ (US)

(72) Inventor: Dallas B. Steele, Phoenix, AZ (US)

( * ) Notice: Subject to any disclaimer, the term of this patent is extended or adjusted under 35 U.S.C. 154(b) by 0 days.

(21) Appl. No.: 17/002,436

(22) Filed: Aug. 25, 2020

(51) Int. Cl.
*A61C 17/10* (2006.01)

(52) U.S. Cl.
CPC .................................. *A61C 17/10* (2019.05)

(58) Field of Classification Search
CPC ..... A61C 17/10; A61C 17/092; A61C 17/096; A61C 17/12; A61C 17/125; A61C 17/08; A61B 1/24
See application file for complete search history.

(56) References Cited

U.S. PATENT DOCUMENTS

| | | | | |
|---|---|---|---|---|
| 4,019,255 | A | * | 4/1977 | Cohen ...................... A61B 1/24 433/93 |
| 4,906,188 | A | * | 3/1990 | Moseley ................ A61C 17/08 433/93 |
| 2005/0004520 | A1 | * | 1/2005 | Lemoine ................ A61C 17/08 604/118 |
| 2009/0035718 | A1 | * | 2/2009 | Coffee ................... A61C 17/04 433/93 |

* cited by examiner

*Primary Examiner* — Heidi M Eide
*Assistant Examiner* — Drew S Folgmann
(74) *Attorney, Agent, or Firm* — Thomas W. Galvani, P.C.; Thomas W. Galvani

(57) ABSTRACT

A cheek retraction device includes a base and a stem extending from the base, the stem for coupling to a vacuum line. Arms extend in opposed directions from the base to opposed grips flanking a working area configured to be disposed over an opened oral cavity. The grips have a plurality of ports coupled in fluid communication to the stem. A trunk extends from the base, between the arms, to in front of the working area. The has a plurality of intakes coupled in fluid communication to the stem.

18 Claims, 6 Drawing Sheets

CHEEK RETRACTION DEVICE

FIELD

The present specification relates generally to medical devices, and more particularly to retraction apparatus in the dental field.

BACKGROUND

Respiratory droplets are a primary vehicle for transmitting respiratory infections. Coughing and sneezing will rapidly disperse a large number of droplets into the air, potentially making airborne a sufficient volume of virus-carrying droplets to infect a person who inhales those droplets. However, even the act of talking and normal breathing will emit virus-carrying droplets, and with prolonged exposure to such talking or breathing, a person may inhale a sufficient number of droplets to become infected.

The above has been well known for some time but has become more acute in the year 2020 due to the pandemic created by the SARS-CoV-2 virus that causes the COVID illness. Governments and individuals, however, have recognized that transmission of this virus—and other viruses—can be mitigated significantly with the use of masks. If both infected and healthy individuals wear masks when close to each other, the spread of disease can be slowed.

Mask wearing is appropriate and practical in many situations, but not all. In the dental setting, a patient's mouth must be open and accessible to the dental staff. A dental hygienist cannot practically work on the mouth of a patient who is wearing a mask. So, dental patients do not wear masks, and this exposes the staff to a risk. Further, hygienists and dentists frequently need to be very close to the patient's mouth and are thus more likely to inhale more of the exhaled air. As such, the staff are even more likely to inhale a sufficient number of virus-carrying droplets to become infected with an illness. An improved method of providing dental services to a patient who may or may not be infected with a communicable respiratory illness is needed.

SUMMARY

A cheek retraction device includes a base and a stem extending from the base, the stem for coupling to a vacuum line. Arms extend in opposed directions from the base to opposed grips flanking a working area configured to be disposed over an opened oral cavity. The grips have a plurality of ports coupled in fluid communication to the stem. A trunk extends from the base, between the arms, to in front of the working area. The has a plurality of intakes coupled in fluid communication to the stem.

The above provides the reader with a very brief summary of some embodiments described below. Simplifications and omissions are made, and the summary is not intended to limit or define in any way the disclosure. Rather, this brief summary merely introduces the reader to some aspects of some embodiments in preparation for the detailed description that follows.

BRIEF DESCRIPTION OF THE DRAWINGS

Referring to the drawings.

DETAILED DESCRIPTION

Figure 1:
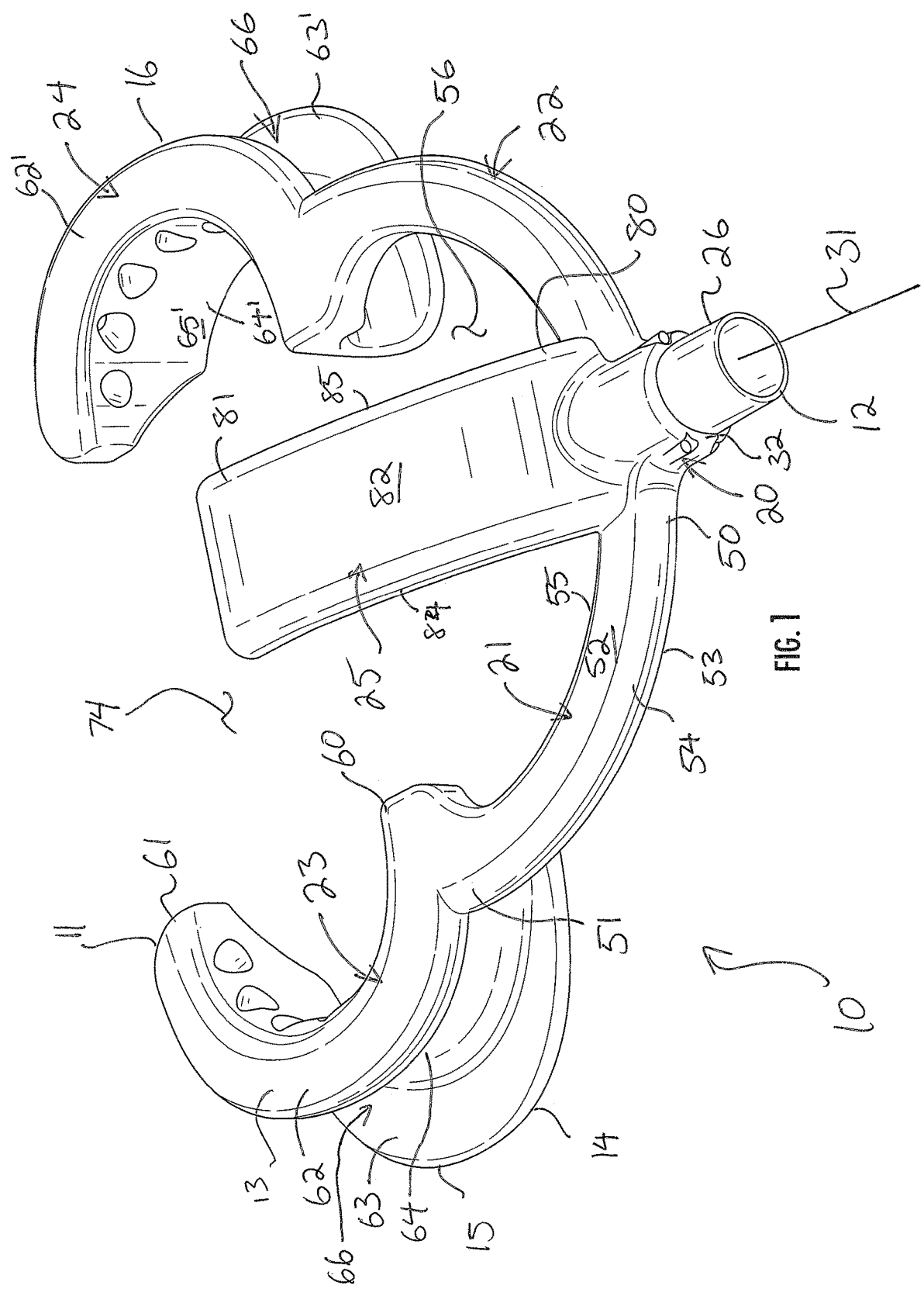
FIG. 1 is a front bottom perspective view of a cheek retraction device.

Reference now is made to the drawings, in which the same reference characters are used throughout the different figures to designate the same elements. Briefly, the embodiments presented herein are preferred exemplary embodiments and are not intended to limit the scope, applicability, or configuration of all possible embodiments, but rather to provide an enabling description for all possible embodiments within the scope and spirit of the specification. Description of these preferred embodiments is generally made with the use of verbs such as "is" and "are" rather than "may," "could," "includes," "comprises," and the like, because the description is made with reference to the drawings presented. One having ordinary skill in the art will understand that changes may be made in the structure, arrangement, number, and function of elements and features without departing from the scope and spirit of the specification. Further, the description may omit certain information which is readily known to one having ordinary skill in the art to prevent crowding the description with detail which is not necessary for enablement. Indeed, the diction used herein is meant to be readable and informational rather than to delineate and limit the specification; therefore, the scope and spirit of the specification should not be limited by the following description and its language choices.

FIG. 1 illustrates a cheek retraction device 10 (hereinafter, the "device 10") in front perspective view. The device 10 has a roughly heart-shaped body symmetric about a sagittal plane (the sagittal plane is identified by two of its corners and the reference character S in FIG. 5). The device 10 has a body with a top 11, an opposed bottom 12, a front 13, an opposed back 14, and opposed left and right sides 15 and 16. The device has a base 20 proximate its bottom 12, and also has opposed left and right arms 21 and 22 projecting from the base 20 and terminating in opposed left and right grips 23 and 24. Moreover, the device includes a trunk 25 that projects upwardly from the base, in front of the arms 21 and 22 and grips 23 and 24.

In use, the grips 23 and 24 and the trunk 25 are disposed in and above a patient's mouth, with the stem 26 below the patient's chin and the grips 23 and 24 retracting the patient's cheeks. The grips 23 and 24 and the trunk 25 are formed with bores or holes, and the body of the device 10 is formed with internal ducts through which air is rapidly drawn to create suction in and above the patient's mouth, thereby drawing away exhaled air from the patient's mouth. A stem 26, extending downwardly from the base 20, is configured to be fit with a vacuum line for drawing such air.

With reference to FIGS. 1, 2, 4, and 5, the base 20 is a hub for the device 10; the arms 21 and 22 extend from the base 20, the trunk 25 projects from the base 20, and the stem 26 depends from the base 20. The base 20 is a short, cylindrical stub. It has an outer diameter 30, and it extends along an axis 31 normal to a transverse or horizontal plane (the horizontal plane is identified by two of its corners and the reference character H in FIG. 3). The axis 31 lies in a sagittal plane extending upward through the device 10. The base 20 is hollow, as is explained later. The base 20 has a circular bottom end which is formed integrally to the stem 26. But the stem 26 has a smaller outer diameter, and so the bottom end defines a shoulder 32 between the base 20 and the stem 26.

The stem 26 extends downwardly from the shoulder 32 and is aligned with the axis 31 and thus the base 20. The stem 26 has an outer diameter 40 which is sized and configured to receive a vacuum line typically used in a dental office, such that the vacuum line can be snugly applied to the stem 26 but still readily removed when the dental procedure is complete. The stem 26 has an open mouth 41 at the bottom 12 of the device 10. When the vacuum line is applied to the stem 26, the open mouth 41 is preferably contained within, or fully encircled by the vacuum line such that the stem 26 and vacuum line are engaged in leakless contact. From the open mouth 41 to the shoulder 32 of the base 20, the outer diameter 40 of the stem 26 is constant. In some embodiments, it enlarges slightly from the open mouth 41 to the shoulder 32.

Figure 2:
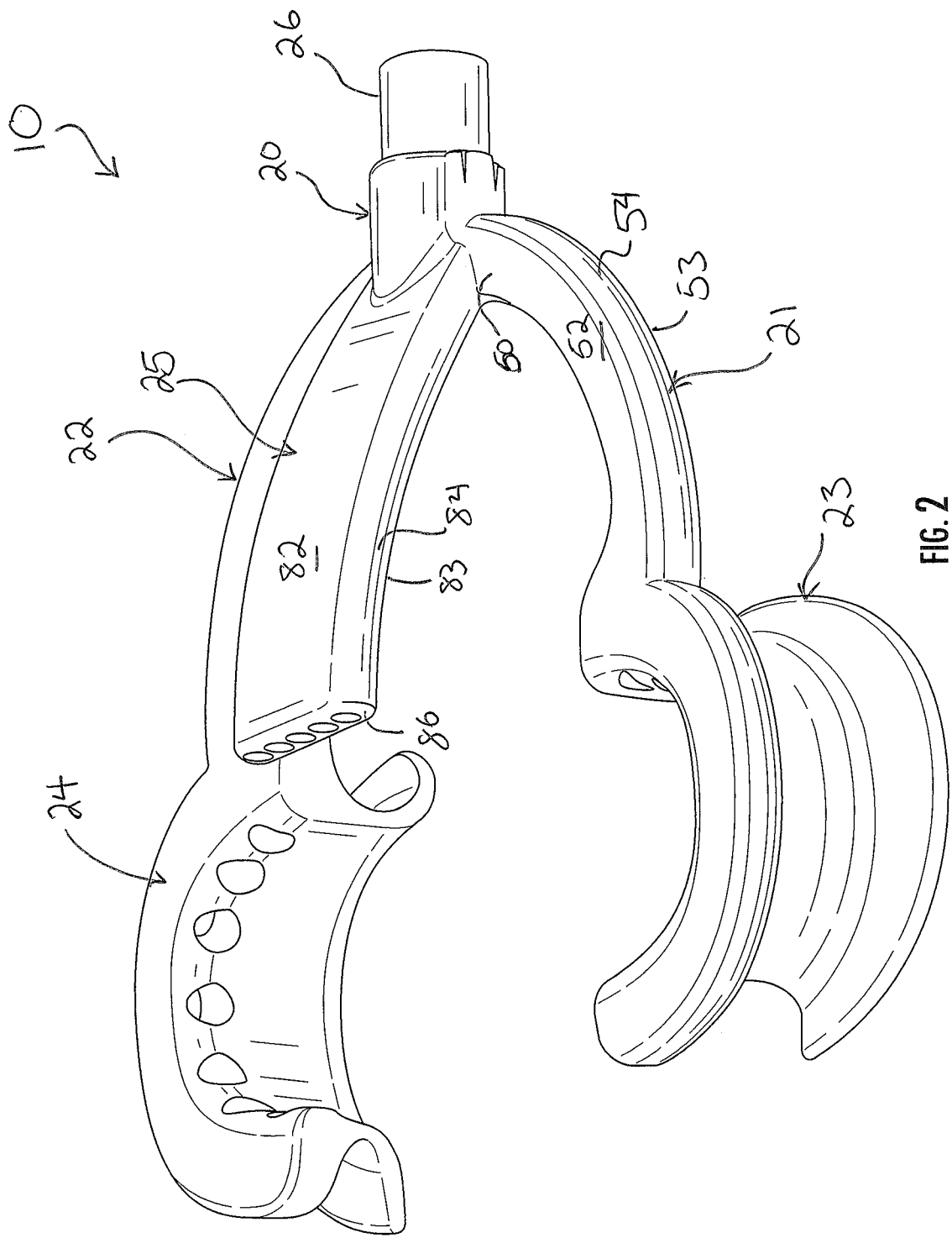
FIG. 2 is a side perspective view of the cheek retraction device of FIG. 1.

With reference now to FIGS. 1 and 2, the arms 21 and 22 extend out from the base 20. The arms 21 and 22 are mirror identical; they have identical constituent elements but are arranged in an opposite fashion about the sagittal plane of symmetry through which the axis A extends. As such, the description herein will refer primarily only to the left arm 21, with the understanding that the description will apply equally to the right arm 22 (though in a mirror identical fashion). The same reference characters are used to identify the identical structural elements and features of both the left and right arms 21 and 22, but those of the right arm 22 are marked with a prime ("'") symbol so as to distinguish them. Further, where drawings do not clearly show the structural element or feature of the left arm 21, reference may be made to the right arm 22 element or feature instead. Since the reference characters are used identically, some identical features will only be identified on one or the other of the arms 21 and 22, for clarity of the illustration.

As part of the device 10 body, the left arm 21 and the right arm 22 are integral, monolithic extensions of the base 20. The left 21 has a proximal end 50 at the base 20 and an opposed distal end 51 away from the base 20. Between the proximal and distal ends 50 and 51, the arm 21 extends arcuately outwardly and upwardly, such that it defines a concave bend shaped to correspond roughly to a patient's face. The arm 21 has a front face 52, an opposed back face 53, and opposed inner and outer faces 54 and 55. The front and back faces 52 and 53 are flat and parallel, while the inner and outer faces 54 and 55 are curved and co-radial. The front and back faces 52 and 53 are also parallel to a coronal or frontal plane which is normal to the sagittal plane through which the axis 31 extends (the frontal plane is identified by two of its corners and the reference character F in FIG. 4). The arm 21 is hollow, as is explained later. The sagittal plane bisects the left arm 21, dividing it equally between front and back halves. Similarly, the right arm 22 has a proximal end 50', a distal end 51', a front face 52', a back face 53', an inner face 54', and an outer face 55'.

The left and right arms 21 and 22 extend in opposed directions from the base to the left and right grips 23 and 24. Together, the left and right arms 21 and 22 define a single chin space 56 below the left and right grips 23 and 24 generally sized and shaped to receive a patient's chin and lower jaw. The arms 21 and 22 are resilient and have a spring bias outward away from each other.

Like the left and right arms 21 and 22, the left and right grips 23 and 24 are mirror identical with respect to the sagittal plane of symmetry through which the axis A extends. As such, the description herein will refer primarily only to the left grip 23, with the understanding that the description will apply equally to the right grip 24 (though in a mirror identical fashion). The same reference characters are used to identify the identical structural elements and features of both the left and right grips 23 and 24, but those of the right grip 24 are marked with a prime ("'") symbol so as to distinguish them. Further, where drawings do not clearly show the structural element or feature of the left grip 23, reference may be made to the right grip 24 feature instead. Since the reference characters are used identically, not all identical features are identified on both grips 23 and 24 for clarity of the illustration.

Still referring primarily to FIGS. 1 and 2, the grip 23 has a proximal end 60 and an opposed distal end 61, between which the grip 23 extends arcuately upwardly in a roughly half-moon shape, such that it defines a concave bend shaped to correspond roughly to a patient's opened mouth. The grip 23 has an outer flange 62, an inner flange 63, and a web 64 extending therebetween. The web 64 defines an inner surface 65 of the grip 23, and both the outer and inner flanges 62 and 63 extend laterally away from the inner surface 65. In this way, the outer flange 62, inner flange 63, and web 64 cooperate to form a U-shaped channel 66. The channel 66 is sized and shaped to receive the lips of a patient's mouth, so as to retract the patient's cheeks during a dental operation. The inner surface 65 is normal to the frontal plane.

Figure 3:
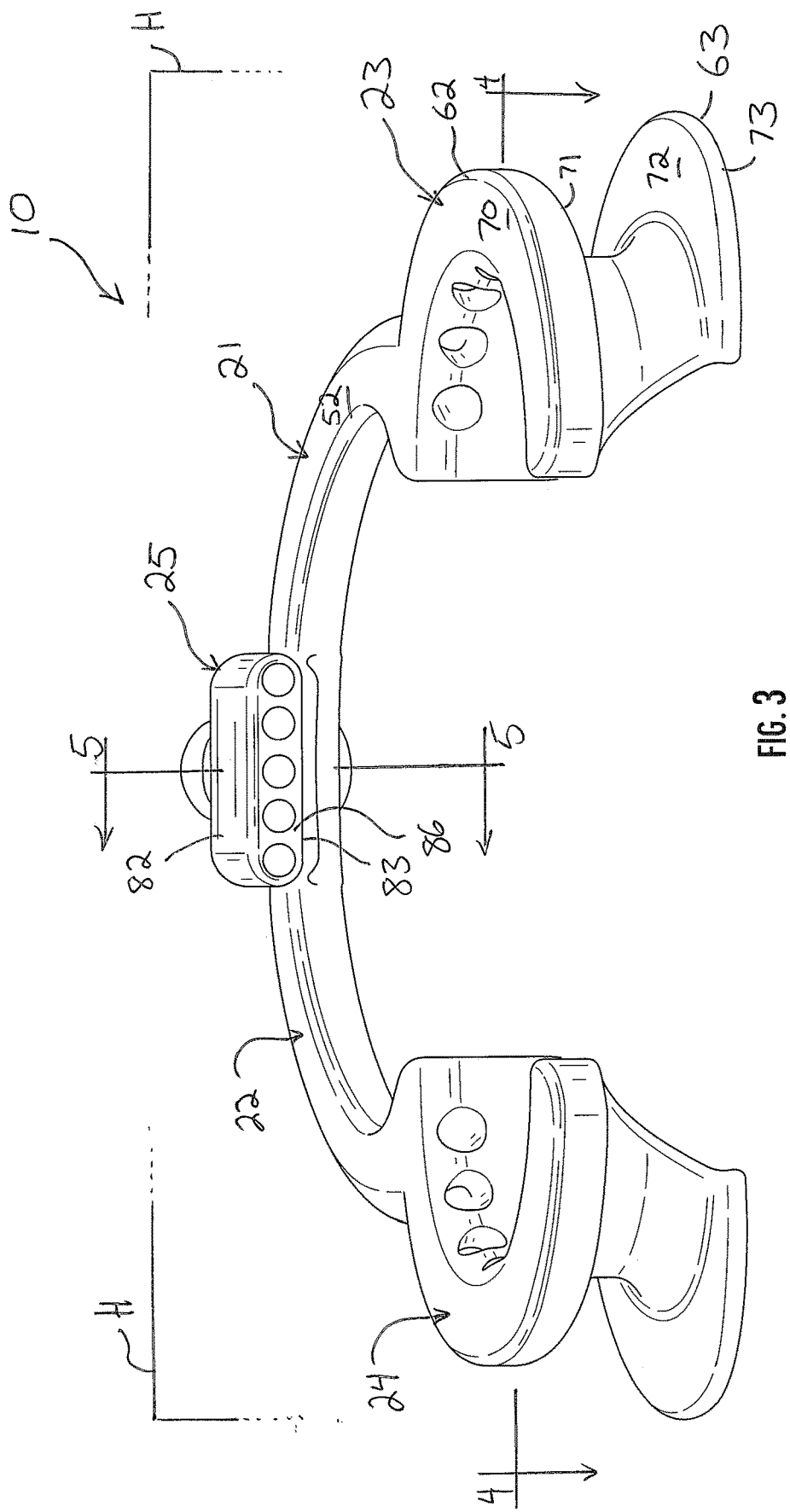
FIG. 3 is a top perspective view of the cheek retraction device of FIG. 1.

Referring now also to FIG. 3, which is a top slight perspective view of the device 10, the outer flange 62 is thicker than the inner flange 63. The outer flange 62 has a front face 70 and an opposed back face 71; similarly, the inner flange 63 has opposed front and back faces 72 and 73. The front face 70 is a contiguous extension of the front face 52 of the left arm 21. The faces 70-73 are all flat and parallel to each other (and to the frontal plane), but they are separated by different distances. The distance between the front face 70 and the back face 71 defines the thickness of the outer flange 62, which is greater than the thickness of the inner flange 63 defined by between the front and back faces 72 and 73. The inner flange 63 is thin and is designed to be disposed within the patient's mouth. In contrast, the outer flange 62 is thicker and disposed outside the patient's mouth. Further, the outer flange 62 is formed with an internal hollow as explained below.

The left and right grips 23 and 24 are bowed in opposed directions. The inner surfaces 65 of the left and right grips 23 and 24 together flank and define a single working area 74 above the left and right arms 21 and 22 generally sized and shaped to be positioned over a patient's opened mouth and oral cavity to provide access thereto with dental instruments.

Referring now to FIGS. 1 and 2 primarily, the trunk 25 extends from the base 20, between the left and right arms 21 and 22 to in front of the working area 74. The trunk 25 is a wide projection, projecting from a proximal end 80 to an opposed distal end 81. The distal end 81 is a blunt free end, cantilevered over and in front of the working area 74. The trunk 25 has a wide front face 82 and a wide, coextensive back face 83. Curved left and right faces 84 and 85 extend therebetween. The front and back faces 82 and 83 are flat between the faces 84 and 85, but the trunk 25 is arcuate: it projects forwardly and upwardly, such that it arches over the working area 74. The distal end 81 is blunt; it terminates in a blunt face 86. The blunt face 86 is oriented parallel to the horizontal plane and normal to the frontal plane.

Figure 4:
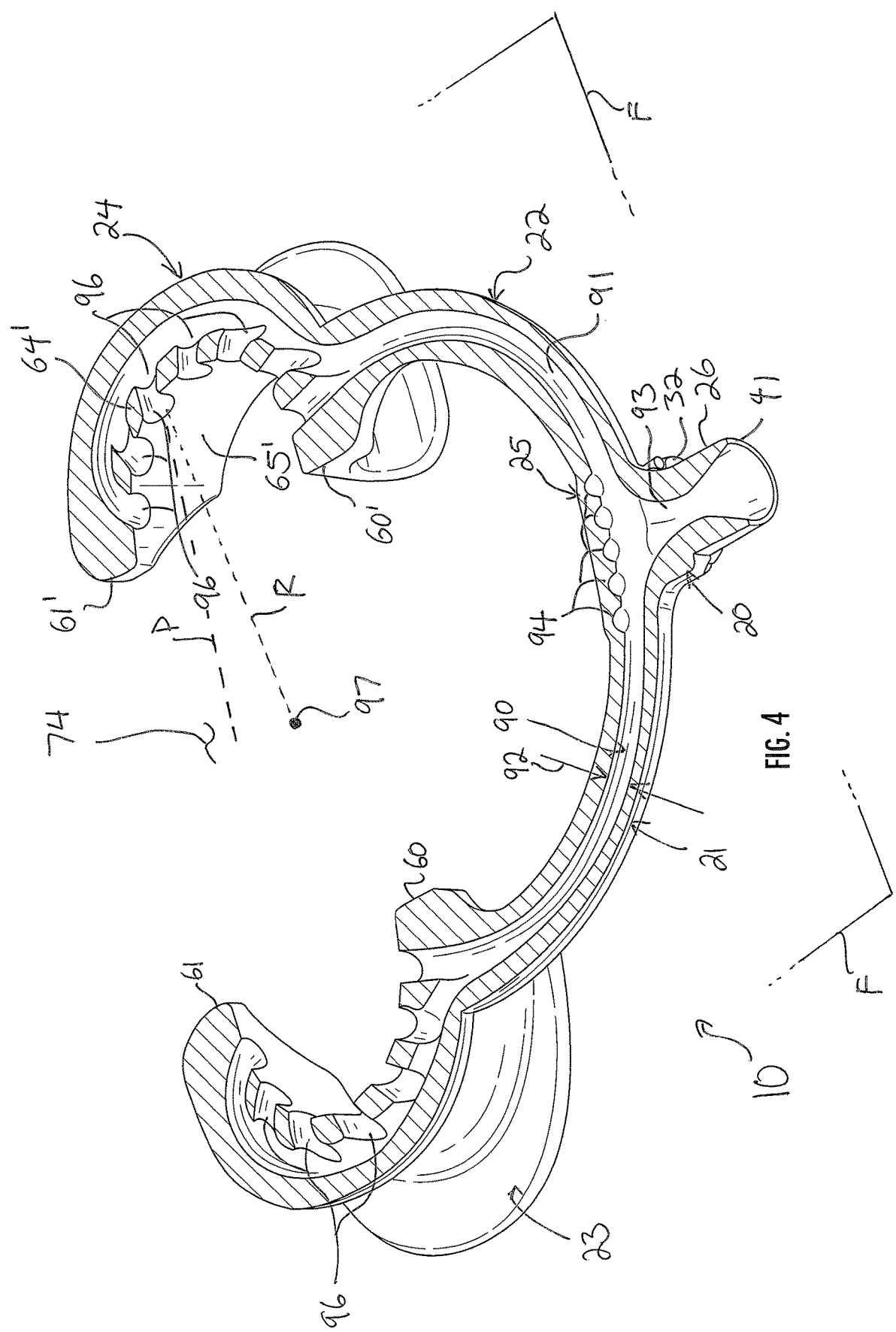
FIG. 4 is a section view of the cheek retraction device of FIG. 1 taken along the line 4-4 in FIG. 3.
Figure 5:
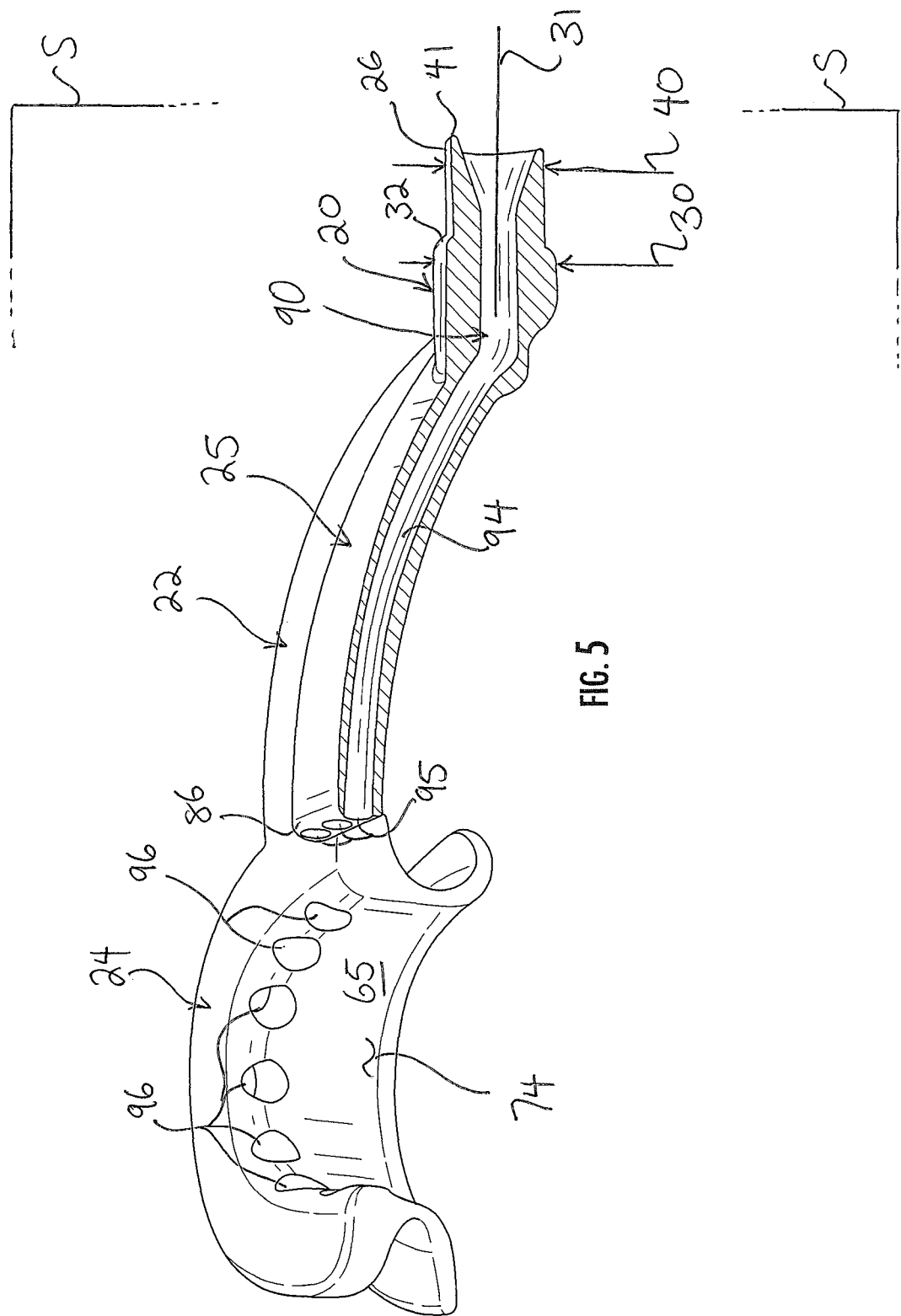
FIG. 5 is a section view of the cheek retraction device of FIG. 1 taken along the line 5-5 in FIG. 3.

In operation, a vacuum line is connected to the stem 26 to draw air through the device 10. An internal airflow channeling 90 formed of a duct, ports, and intakes are formed in the device 10 to accommodate this. The channeling 90 is shown in FIGS. 4 and 5. The channeling 90 includes a main duct 91 extending continuously from the left grip 23, through the left arm 21, through the base 20, through the right arm 22, and through to the right grip 24. The duct 91 is a hollow channel or tunnel in these elements. The duct 91 has an inner diameter 92 which is constant and the same in the left and right arms 21 and 22.

At the base 20 and stem 26, the duct 91 includes a nozzle 93. The nozzle 93 stems from the duct and is directed normal to the orientation of the duct 91 between the left and right arms 21 and 22. The nozzle 93 extends away from the duct 91 and then constricts at the shoulder 32 before enlarging at the open mouth 41 of the stem 26. The shoulder 32 therefore defines a constriction point of the duct 91.

Opposite the nozzle 93, a plurality of intakes 94 are internally coupled in fluid communication to the duct 91, and thus also in fluid communication to the nozzle 93 in the base 20 and stem 26. These intakes 94 are long conduits or tunnels which extend up through the trunk. In the preferred embodiment of FIG. 4, there are five intakes 94. These five intakes 94 are unique and separated; they preferably are not connected to each other along their lengths. FIG. 5 is a section view bisecting the device 10 and shows the entire length of the middle intake 94 from the duct 91 and nozzle 93 to inlets 95 formed in the blunt face 86 of the trunk 25. As can be seen in FIG. 5, the inlets 95—and the intakes 94 terminating in the inlets 95—are arranged in a plane which is parallel to the frontal plane: they are directed outwardly normal to the blunt face 86. As such, air is drawn into the intakes 94 on a first plane away from the working area 74.

At the left and right grips 23 and 24, the ducts terminate in ports 96. Turning back to the section view of FIG. 4, the ports 96 are illustrated well. Each port 96 is a bore formed entirely through the web 64, joining the duct 91 in fluid communication with the open working area 74. The ports 96 are all transverse with respect to the inner surface; each extends through the web 64 at an angle. For better explanation, FIG. 4 illustrates a point in the working area, marked with the reference character 97, which identifies a geometric center of the working area. There are an infinite number of radii extending from the inner surface 65 to this center 97. The ports 96, however, are discretely spaced apart across the web 64 and inner surface 65 of the web 64, and so there is a separate and distinct radius extending from each port 96 to the center 97. One such radius R is shown in broken line in FIG. 4. Each port 96 has an orientation defined by an axis extending centrally through the port 96. One such axis P is shown in FIG. 4 in broken line. The line P—the orientation of the port 96, is misaligned with the radius R extending from the port 96 to the center 97. This is true of all the ports 96. Further, the ports 96 each have different orientations: the ports 96 near the proximal end 60' of the right grip 24 have an orientation generally toward the distal end 61', and the ports 96 near the distal end 61' have an orientation generally toward the proximal end 60'. Between these two ends, orientations change a bit with each port 96. This arranges the orientations of all the ports 96 on either the left grip 23 or right grip 24 in a spiral pattern, and so the air drawn into the ports 96 on either the left grip 23 or the right grip 24 is drawn in a spiral pattern, which serves to expand the suction of the ports 96 to cover the entire working area 74. Referring now again to FIG. 5, it is seen that the ports 96 are arranged in a plane, parallel to the frontal plane. Thus, they are parallel to the plane of the intakes 94 and inlets 95, but are offset or spaced apart from that plane. As such, the suction produced by the ports 96 establishes a first plane of suction, and the suction produced by the intakes 94 produces a second plane of suction.

Figure 6:
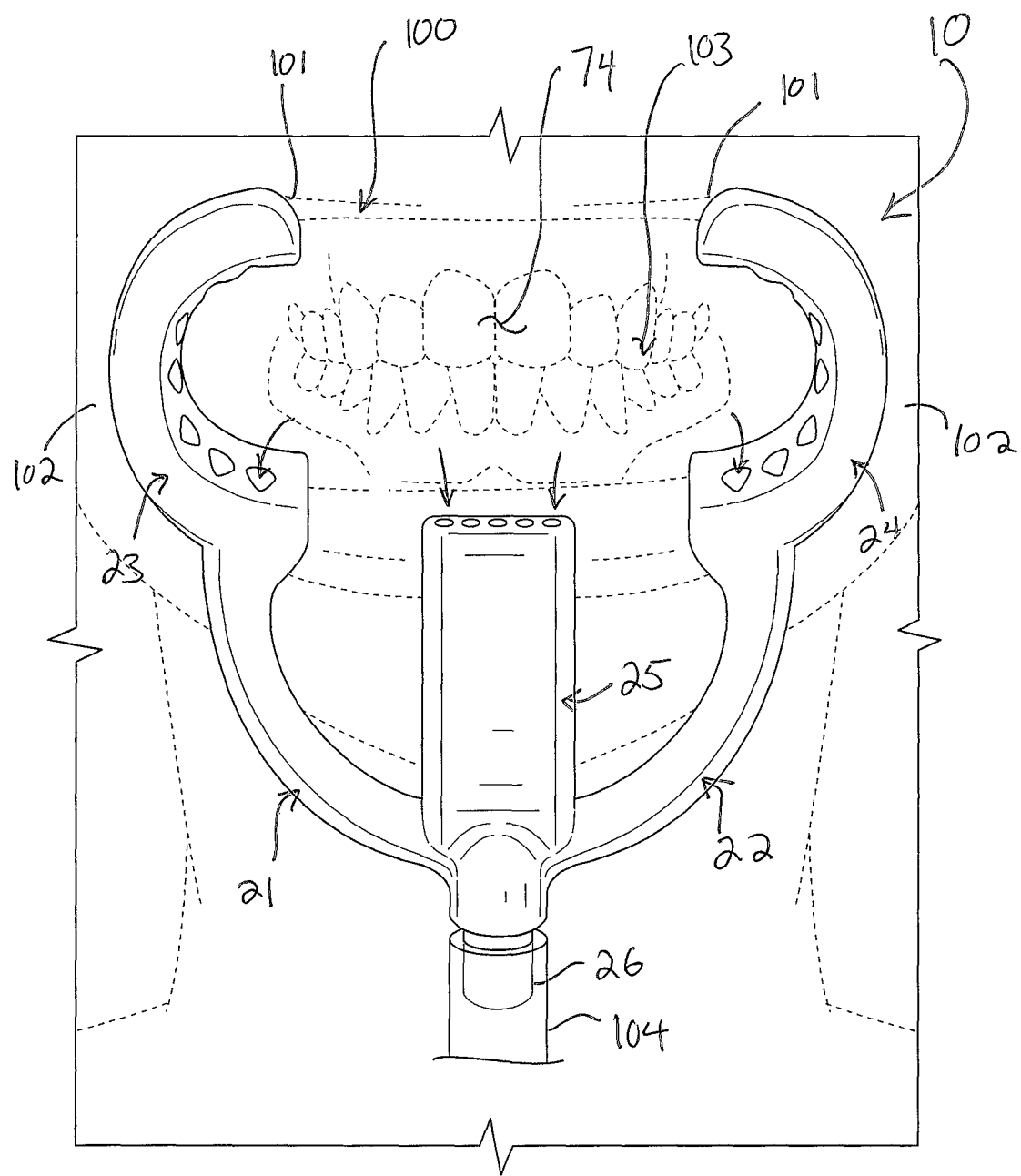
FIG. 6 is a front view of the cheek retraction device of FIG. 1 as it would appear in use in a patient's mouth.

With reference now to FIG. 6, the device 10 is shown in use in a patient's mouth 100. The lips 101 are placed into the U-shaped channels 66 and 66' of the left and right grips 23 and 24. The spring force of the left and right arms 21 and 22 draws the lips 101 and cheeks 102 away, thereby exposing the patient's oral cavity 103 in the working area 74 and providing the dentist access to the oral cavity 103. A vacuum line 104 is coupled to the stem 26. When the vacuum is turned on, air is drawn in through the intakes 94 and the inlets 95 and through the ports 96, across the working area at two different levels, to effectively draw all droplets exhaled by the patient into the vacuum line. In this manner, the dental staff is protected from inadvertent infection during a dental procedure.

A preferred embodiment is fully and clearly described above so as to enable one having skill in the art to understand, make, and use the same. Those skilled in the art will recognize that modifications may be made to the description above without departing from the spirit of the specification, and that some embodiments include only those elements and features described, or a subset thereof. To the extent that modifications do not depart from the spirit of the specification, they are intended to be included within the scope thereof.

What is claimed is:

1. A cheek retraction device for retracting cheeks of a patient away from an oral cavity of the patient and drawing air from the oral cavity, the cheek retraction device comprising:
   a base and a hollow stem extending monolithically from the base, wherein the stem is for coupling to a vacuum line which, when so coupled, provides suction through the cheek retraction device to draw air out of the oral cavity, internally through the cheek retraction device, and into the vacuum line;
   two arms, each formed monolithically to the base, extending in opposed directions from the base to opposed grips flanking a working area configured to be disposed over the opened oral cavity, wherein the grips are formed monolithically to the respective arms and have a plurality of ports coupled in fluid communication to the stem, wherein when the cheek retraction device is used with the patient, the grips retract and retain the cheeks, the working area is disposed over the oral cavity, and the ports are directed into the working area to draw air therefrom;
   a common duct extending continuously through the cheek retraction device, from the ports, internally through the opposed grips, the opposed arms, the base, and the stem to thereby join the ports in fluid communication with the stem; and
   a trunk extending from the base, between the arms, to in front of the working area, the trunk having a plurality of intakes coupled in fluid communication to the common duct in the stem.

2. The cheek retraction device of claim 1, wherein the grips have inner surfaces and the ports are formed through the inner surfaces.

3. The cheek retraction device of claim 1, wherein each in-take-port is transverse to a radius extending into a center of the working area from the respective port.

4. The cheek retraction device of claim 1, wherein each of the intakes in the trunk is a unique conduit extending separately through the trunk to the duct.

5. The cheek retraction device of claim 1, wherein the duct has a constriction point at the stem.

6. The cheek retraction device of claim 1, wherein the trunk terminates in a blunt end and the intakes are formed in the blunt end.

7. The cheek retraction device of claim 1, wherein the intakes of the trunk are parallel to a plane extending through the ports.

8. A cheek retraction device for retracting cheeks of a patient away from an oral cavity of the patient and drawing air from the oral cavity, the cheek retraction device comprising:
 a base and a hollow stem extending monolithically from the base, wherein the stem is for coupling to a vacuum line which, when so coupled, provides suction through the cheek retraction device to draw air out of the oral cavity, internally through the cheek retraction device, and into the vacuum line;
 two arms, each formed monolithically to the base, extending in opposed directions from the base to opposed grips, the arms biasing the grips apart from each other;
 the grips having inner surfaces which cooperate to bound and define a working area configured to be disposed over the oral cavity, wherein the grips are formed monolithically to the respective arms and have a plurality of ports coupled in fluid communication to the stem, wherein when the cheek retraction device is used with the patient, the grips retract and retain the cheeks, the working area is disposed over the oral cavity, and the ports are directed into the working area to draw air therefrom; and
 a common duct extending continuously through the cheek retraction device, from the ports, internally through the opposed grips, the opposed arms, the base, and the stem to thereby join the ports in fluid communication with the stem; and
 a trunk extending from the base, between the arms, to in front of the working area, the trunk terminating in a plurality of intakes coupled in fluid communication to the common duct in the stem.

9. The cheek retraction device of claim 8, wherein each intake-port is transverse to a radius extending into a center of the working area from the respective port.

10. The cheek retraction device of claim 8, wherein the duct has a constriction point at the stem.

11. The cheek retraction device of claim 8, wherein each of the intakes is a unique conduit extending separately through the trunk to the duct.

12. The cheek retraction device of claim 8, wherein the trunk terminates in a blunt end and the intakes are formed in the blunt end.

13. The cheek retraction device of claim 8, wherein the intakes are parallel to a plane extending through the ports.

14. A cheek retraction device for retracting cheeks of a patient away from an oral cavity of the patient and drawing air from the oral cavity, the cheek retraction device comprising:
 a base, a hollow stem extending monolithically from the base, and arms, each formed monolithically to the base, extending away from the base to opposed grips, the arms biased apart from each other;
 each grip is formed monolithically to the respective arms and comprises an outer flange, an inner flange, and a web extending therebetween to define a U-shaped channel for retracting the cheeks of the patient;
 a trunk extending from the base to above and between the arms; and
 an internal airflow channeling within the device comprising a common duct extending continuously through the cheek retraction device from the base and stem through the arms to the grips, ports formed through the web of each grip and joined in fluid communication to the common duct, and inlets in the trunk joined in fluid communication to the common duct.

15. The cheek retraction device of claim 14, wherein each port is transverse to a radius extending into a center of the working area from the respective port.

16. The cheek retraction device of claim 14 wherein each of the intakes is a unique conduit extending separately through the trunk to the duct.

17. The cheek retraction device of claim 14, wherein the trunk terminates in a blunt end and the intakes are formed in the blunt end.

18. The cheek retraction device of claim 14, wherein the intakes are parallel to a plane extending through the ports.

\* \* \* \* \*